United States Patent [19]

Shaw et al.

[11] 4,250,054
[45] Feb. 10, 1981

[54] CATALYSTS FOR PRODUCING UNSATURATED ALIPHATIC ACIDS

[75] Inventors: Wilfrid G. Shaw, Lyndhurst; Ernest C. Milberger, Solon; Serge R. Dolhyj, Parma, all of Ohio

[73] Assignee: The Standard Oil Company (Ohio), Cleveland, Ohio

[21] Appl. No.: 691,691

[22] Filed: Jun. 1, 1976

[51] Int. Cl.$^3$ .............. B01J 23/10; B01J 23/22; B01J 23/28; B01J 27/18
[52] U.S. Cl. .................... 252/437; 252/435; 252/462; 562/534; 562/535
[58] Field of Search ............ 252/437, 462, 435; 260/530 N

[56] References Cited

U.S. PATENT DOCUMENTS 3,956,377  5/1976  Dolhyj et al. .............. 252/462 X

FOREIGN PATENT DOCUMENTS 2448804  4/1975  Fed. Rep. of Germany ...... 260/530 N
2550440  5/1976  Fed. Rep. of Germany ...... 260/530 N

*Primary Examiner*—W. J. Shine
*Attorney, Agent, or Firm*—David J. Untener; Herbert D. Knudsen; Larry W. Evans

[57] ABSTRACT

The present invention relates to a process for the production of unsaturated aliphatic acids and the catalyst therefor, by the vapor phase oxidation of the corresponding unsaturated aliphatic aldehydes with molecular oxygen, optionally in the presence of steam, in the presence of an oxidation catalyst consisting of the oxides of the elements molybdenum, vanadium, tungsten and lanthanum, and optionally one or more of the oxides of the elements manganese, iron, copper, aluminum, cobalt, nickel, phosphorus, zinc, bismuth, silver, cadmium, niobium, arsenic, chromium, the alkali and the alkaline earth elements.

3 Claims, No Drawings

CATALYSTS FOR PRODUCING UNSATURATED ALIPHATIC ACIDS

BACKGROUND OF THE INVENTION

Catalyst compositions similar to those of the present invention are known for the oxidation of acrolein to acrylic acid. For example, the disclosure in U.S. Pat. No. 3,567,773 shows catalyst compositions containing the elements of molybdenum, vanadium and tungsten, and German Pat. No. 2,456,100 discloses catalysts having the composition of molybdenum, vanadium and tungsten in combination with such elements as copper, cobalt and iron. However the catalyst composition of the present invention has heretofore not been disclosed.

THE INVENTION

The present invention relates to an improved process for producing olefinically unsaturated carboxylic acids from the corresponding unsaturated aldehydes and to the catalyst composition utilized therefor. More specifically, the present invention relates to a vapor phase process for producing acrylic acid or methacrylic acid from acrolein and methacrolein, respectively, by oxidation of the unsaturated aldehydes with molecular oxygen, optionally in the presence of steam, and in the presence of an oxidation catalyst having the empirical formula:

$$Mo_a V_b W_c La_d X_e O_f$$

wherein
X is one or more of the elements selected from the group consisting of manganese, iron, copper, zinc, aluminum, cobalt, nickel, phosphorus, cadmium, bismuth, silver, niobium, arsenic, chromium, alkali and alkaline earth elements, and wherein
the number of atoms of each element present is represented by a through f, wherein
a is a number from 6 to 18;
b is a number from 0.1 to 10;
c is a number from 0.1 to 6;
d is a number from 0.01 to 5;
e is a number from 0 to 5; and
f is a number that satisfies the valence requirements of the other elements present.

Preferred catalysts are those wherein a is between 9 and 15; b is between 0.5 and 5; c is between 0.5 and 3; d is between 0.05 and 1; and e is between 0 and 1. The elements are present in these catalytic composition in the form of their oxides or oxide complexes.

In addition to the active catalytic ingredients, the catalysts of the invention may contain a support material. Suitable support materials include silica, alumina, zirconia, silicon carbide, boron phosphate and the like. A preferred support material is alundum.

The catalysts of this invention are highly effective for oxidation reactions such as the oxidation of butadiene to maleic anhydride and the oxidative esterification of unsaturated aldehydes to the corresponding unsaturated ester. Preferred among these oxidative reactions is the production of unsaturated acids from the corresponding unsaturated aldehyde, and more specifically the catalysts of the invention are capable of very selectively oxidizing acrolein to acrylic acid at low temperatures with little or no acetic acid production.

The oxidation of unsaturated aldehydes to obtain the corresponding acid is well known in the art. Basically, the invention, with respect to the process, is the use of the new catalyst within the parameters of the known art process.

The known process involves the contacting of the unsaturated aldehyde with molecular oxygen in the presence of steam at a temperature of about 200° to about 500° C. The ratio of the reactants may vary widely, with molar ratios of molecular oxygen to aldehyde of about 0.5 to about 5 normally being employed. Molecular oxygen is most conveniently added as air. The amount of steam may vary widely from the small amount generated in the reaction to 20 or more moles of steam per mole of aldehyde. In the preferred practice of the invention, about 1 to about 10 moles of steam are added to the reactant feed.

The reaction may be conducted in a fixed-bed or fluid-bed reactor or forms thereof, using atmospheric, superatmospheric or subatmospheric pressure. The apparent contact time may vary considerably, with contact times of a fraction of a second to 20 seconds or more normally being employed.

As noted above, catalysts very similar to the catalysts of the invention are known, see for example U.S. Pat. No. 3,567,773, and thus catalysts of this general type can readily be prepared by persons of ordinary skill in the art.

Normally, the catalysts of the invention are prepared by mixing the catalyst ingredients in the proper proportions in an aqueous mixture, drying the resulting aqueous slurry and calcining the product. The ingredients going into the preparation of the catalysts can be the oxides, halides, nitrates, acetates, or other salts of the particular compound added. If a support is used, the material comprising the support is usually incorporated into the catalyst along with the other ingredients. After the catalyst ingredients have been combined to form an aqueous slurry, the slurry is evaporated to dryness, and the dried solid obtained is heated in the presence of air at temperatures between about 200° and 600° C. This calcination can take place outside of the catalytic reactor or an in situ activation can be utilized.

There are a number of preparations that can be used to make desirable catalysts of the invention. A preparation used in the examples is shown in the Specific Embodiments, but it is not to be construed that the method of preparation is limited to the preparation described.

SPECIFIC EMBODIMENTS

Catalyst Preparation

The catalyst of Comparative Example A and the catalysts of Examples 1-4 which are representative of the present invention were prepared according to the following procedure.

COMPARATIVE EXAMPLE A

Catalyst $Mo_{12}V_3W_{1.2}O_{47.1}$

To 250 cc of hot distilled water was added 6.16 g of ammonium metavanadate. After this reagent was dissolved with heating and stirring, 5.84 g of ammonium metatungstate and 37.21 g of ammonium heptamolybdate were added and readily dissolved. The solution was evaporated to near dryness with continual heating and stirring, and the contents were then placed in a drying oven at approximately 120° C. for 16 hours. The dried material was crushed and ground to pass through a 50 mesh screen. A sufficient amount of powder was employed to coat 3/16" alundum spheres to achieve a twenty weight percent coating on the spheres. The coated spheres were then dried at 120° C. for three hours and then activated by heat treating at 370° C. for two hours.

EXAMPLE 1

Catalyst $Mo_{12}V_3W_{1.2}La_{0.5}O_{47.8}$

The procedure of Comparative Example A was repeated using the same quantities of the same reagents followed by the addition of 1.43 g of lanthanum oxide ($La_2O_3$) and the catalyst completed as described.

EXAMPLE 2

Catalyst $Mo_{12}V_3W_{1.2}La_{0.5}Co_{0.1}O_{48.0}$

The procedure of Composition A was repeated using 4.44 g of ammonium metavanadate, 4.21 g of ammonium metatungstate, and 26.84 g of ammonium heptamolybdate, followed by the addition of 1.03 g of lanthanum oxide and 0.315 g of cobalt acetate, and the catalyst completed as described.

EXAMPLE 3

Catalyst $Mo_{12}V_3W_{1.2}La_{0.5}Cu_{0.2}O_{48.0}$

The procedure of Composition A was repeated using 4.43 g of ammonium metavanadate, 4.20 g of ammonium metatungstate, 26.75 g of ammonium heptamolybdate, followed by the addition of 1.03 g of lanthanum oxide and 0.50 g of cupric acetate, and the catalyst completed as described.

EXAMPLE 4

Catalyst $Mo_{12}V_3W_{1.2}La_{0.5}Mn_{0.1}O_{48.0}$

The procedure of Composition A was repeated using 4.45 g of ammonium metavanadate, 4.22 g of ammonium metatungstate, 26.85 g of ammonium heptamolybdate, followed by the addition of 1.03 g of lanthanum oxide, and 0.31 g of manganese acetate, and the catalyst completed as described.

The catalysts prepared above were placed in a fixed-bed reactor constructed of 1.0 cm.-inside diameter stainless steel tubing having a reaction zone of 20 c.c. The reactor was heated in a split block furnace. The reactor was fed with a mixture of acrolein/air/nitrogen/steam in the molar ratio of 1/8.5/2.5/6. The reaction was conducted at atmospheric pressure, and an apparent contact time was two seconds. The temperatures of the surrounding block employed in the reactions are given in Table I, and the results given in the Table are in terms of the following definitions:

$$\text{Percent Conversion} = \frac{\text{Moles of acrolein reacted}}{\text{Moles of acrolein fed}} \times 100$$

$$\text{Percent Single Pass Yield} = \frac{\text{Moles of product recovered}}{\text{Moles of acrolein fed}} \times 100$$

$$\text{Percent Selectivity} = \frac{\text{Moles of acrylic acid recovered}}{\text{Moles of acrolein reacted}} \times 100$$

The improved conversions of acrolein to acrylic acid obtained with the catalyst compositions of the present invention are readily apparent by the direct comparison of Examples 1–4 with Comparative Example A which represents a catalyst composition of the prior art.

In the same manner as shown by the examples above, other catalysts of the invention containing different amounts of lanthanum and different optional elements, such as iron, zinc, aluminum, chromium, and the like are used to produce acrylic acid.

Also using the catalysts of the present invention, maleic anhydride, methacrylic acid or acrylates are produced by known oxidation reactions.

TABLE I

| | | Oxidation of Acrolein to Acrylic Acid | | | | |
|---|---|---|---|---|---|---|
| | | Reaction | % Conv. of | [Corrected[2] % Single Pass Yield of] | | % Selec. to |
| Example No. | Catalyst Composition[1] | Temp., °C. | Acrolein | Acrylic Acid | Acetic Acid | Acrylic Acid |
| Comp. A | $Mo_{12}V_3W_{1.2}O_{47.1}$ | 318 | 98.1 | 81.4 | 2.8 | 83.0 |
| 1 | $Mo_{12}V_3W_{1.2}La_{0.5}O_{47.8}$ | 319 | 97.0 | 84.3 | 2.4 | 86.9 |
| 2 | $Mo_{12}V_3W_{1.2}La_{0.5}Co_{0.1}O_{48.0}$ | 342 | 98.5 | 87.7 | 2.6 | 89.0 |
| 3 | $Mo_{12}V_3W_{1.2}La_{0.5}Cu_{0.2}O_{48.8}$ | 320 | 99.9 | 91.3 | 2.1 | 91.3 |
| 4 | $Mo_{12}V_3W_{1.2}La_{0.5}Mn_{0.1}O_{48.0}$ | 348 | 97.0 | 85.4 | 2.7 | 88.0 |

[1]20% active catalyst component coated on 3/16" Alundum spheres.
[2]Corrected to 100% carbon balance.

We claim:

1. A catalyst having the empirical formula:

$$Mo_aV_bW_cLa_dX_eO_f$$

wherein
X is one or more of the elements selected from the group consisting of manganese, iron, copper, zinc, aluminum, cobalt, nickel, phosphorus, cadmium, bismuth, silver, niobium, arsenic, chromium, and the alkali and the alkaline earth elements; and wherein
the number of atoms of each element present i represented by a–f;

wherein
a is a number from 6–18;
b is a number from 0.1–10;
c is a number from 0.1–6;
d is a number from 0.01–5;
e is a number greater than 0, up to 5;
f is a number that has satisfied the valence requirements of the other elements present; and wherein the catalyst does not contain cerium.

2. The catalyst of claim 1 wherein a=9 to 15; b=0.5 to 5; c=0.5 to 3; d=0.05 to 1; e=a number greater than 0, up to 1; and f is a number that satisfies the valence requirements of the other elements present.

3. A catalyst composition consisting essentially of an oxide complex of molybdenum, vanadium, tungsten, lanthanum and at least one element selected from the group consisting of manganese, iron, copper, aluminum, cobalt, nickel, bismuth, silver, phosphorus, zinc, cadmium, niobium, arsenic, chromium, the alkali metals and the alkaline earth metals.

* * * * *

Notice of Adverse Decision in Interference

In Interference No. 100,908, involving Patent No. 4,250,054, W. G. Shaw, E. C. Milberger and S. R. Dolhyj, CATALYSTS FOR PRODUCING UNSATURATED ALIPHATIC ACIDS, final judgment adverse to the patentees was rendered Jan. 26, 1983, as to claim 1.

[*Official Gazette May 17, 1983.*]